United States Patent [19]

Whitehead et al.

[11] 4,376,440
[45] Mar. 15, 1983

[54] SANITARY NAPKIN WITH ADHESIVE ATTACHMENT MEANS

[75] Inventors: Howard A. Whitehead; Robert J. Roeder; Herbert E. Grube, all of Appleton, Wis.

[73] Assignee: Kimberly-Clark Corporation, Neenah, Wis.

[21] Appl. No.: 175,300

[22] Filed: Aug. 5, 1980

[51] Int. Cl.³ .............................................. A61F 13/16
[52] U.S. Cl. .................................................... 604/387
[58] Field of Search ............... 128/284, 285, 287, 290, 128/DIG. 30, 156

[56] References Cited

U.S. PATENT DOCUMENTS

| 2,295,016 | 9/1942 | Schribner | 128/DIG. 30 |
| 3,670,731 | 6/1972 | Harmon | 128/287 |
| 3,881,490 | 5/1975 | Whitehead et al. | 128/287 |
| 3,890,974 | 6/1975 | Kozak | 128/287 |
| 3,913,580 | 10/1975 | Ginocchio | 128/290 W |
| 4,117,184 | 9/1978 | Erickson et al. | 128/156 |

Primary Examiner—Richard J. Apley
Assistant Examiner—T. J. Wallen
Attorney, Agent, or Firm—Howard Olevsky; R. Jonathan Peters; William D. Herrick

[57] ABSTRACT

A sanitary napkin having a pressure sensitive adhesive applied on the underside of a moisture impervious baffle for attachment to undergarments is provided. The adhesive is geometrically shielded without the presence of a release liner.

13 Claims, 3 Drawing Figures

SANITARY NAPKIN WITH ADHESIVE ATTACHMENT MEANS

FIELD OF THE INVENTION

This invention relates to a sanitary napkin and particularly to a sanitary napkin having pressure sensitive adhesive disposed on the bottom of a fluid impervious baffle for attachment to undergarments.

BACKGROUND OF THE INVENTION

Recently sanitary napkins having pressure sensitive adhesive applied to the underside of the fluid impervious baffle have become increasingly popular. These napkins have the conventional components, i.e. a moisture absorbent matrix and a fluid impervious baffle material. The absorbent component may be wrapped with a fluid pervious outer wrap to preserve the integrity of the absorbent and this wrap may be attached by adhesion or fusing to the bottom of the pad or to either the undergarment or pad facing side of the baffle. The adhesive, whether applied to the baffle or an outer wrap, invariably has a release paper attached thereto. Prior to use the release paper is peeled from the adhesive and the adhesive surface is attached to the undergarment. The release strip is then discarded. The release strip functions to prevent the premature and unwanted adhesion of the pressure sensitive adhesive to materials other than undergarments such as other sanitary napkins. As a secondary function, the release liner inhibits the aging of the adhesive because it provides less surface exposure to environmental aging factors such as oxygen. Release liners, however, add substantially to the cost of the sanitary napkin due to the cost of the material and the additional process step needed to apply it. Also, there is the problem of disposal of the liner. These release liners are typically thermoplastic or silicone treated paper and, in either instance, they are not flushable and not easily biodegradable.

SUMMARY OF THE INVENTION

This invention provides a sanitary napkin with pressure sensitive adhesive means for attachment to undergarments such that release liners used to shield the adhesive and prevent premature adherence are not needed. This is accomplished in a variety of ways but broadly the concept of this invention involves utilizing a baffle which is characterized by recessed areas containing adhesives which have an enhanced aging resistance when compared to conventional pressure sensitive adhesives utilized for undergarment attachment. The adhesive component is shielded by the geometry of the baffle until such time as the sanitary napkin is attached to the undergarment. The conforming of the baffle to the undergarment for attachment exposes the surface of the adhesive to the undergarment.

DETAILED DESCRIPTION OF THE INVENTION

This invention can be better understood by reference to the drawings in which

Figure 1:
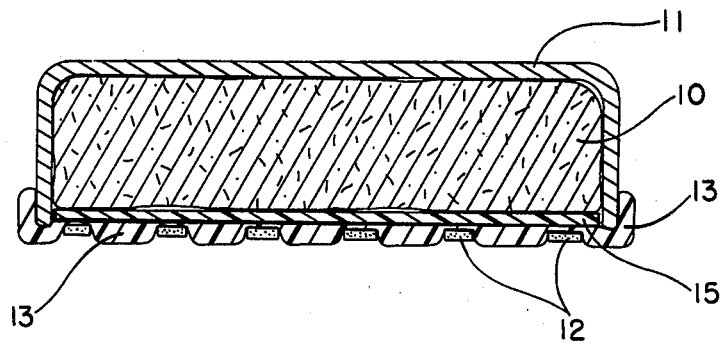
Figure 2:
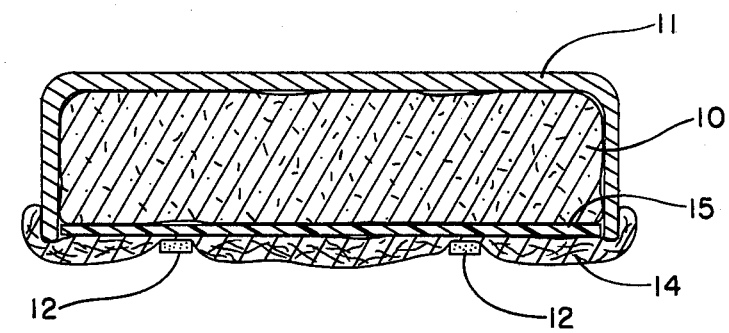
Figure 3:
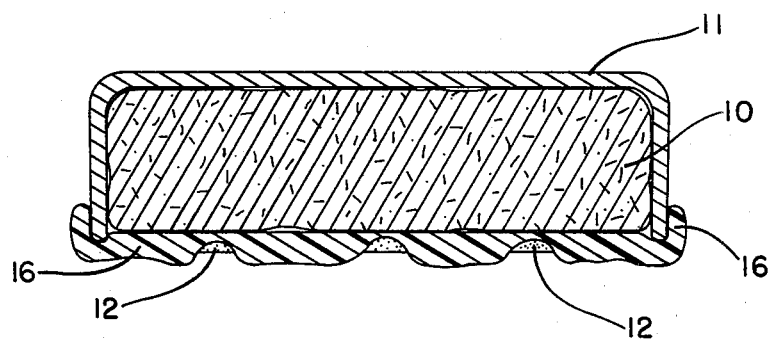

FIGS. 1, 2, and 3 are cross-sectional end views of three embodiments of a sanitary napkin having the baffle configuration according to this invention in which the same numerals are used for the same parts.

For purposes of this invention, increased resistance to aging is defined as the ability of an adhesive to satisfactorily adhere to undergarments after long term storage. Specifically, this is defined as the reduction of not greater than 25% of the adhesive strip after one year of storage as defined by the Peel-Adhesion test.

The Peel-Adhesion test measures the amount of force necessary to separate a strip of cotton which has been placed in contact with a backing material having an adhesive surface coated thereon. After adhesive contact has occurred, a force of 2 kPa is applied to the two sheets and is maintained for 60 minutes at 24° C. The strip containing the adhesive and the cotton strip are then separated at a constant rate of 8 cm/min.

It is currently preferred that the adhesive have a minimum value of 40 grams separation force and, therefore, the adhesive after one year of storage has a minimum separation force of 30 grams as defined by this test.

Suitable types of adhesives which may be utilized to accomplish the teachings of this invention may be defined broadly as water emulsion adhesives and reactive adhesive prepolymers. A suitable water emulsion adhesive is a copolymer of vinyl acetate and 2-ethylhexyl acrylate dispersed in water. An example of a suitable commercial adhesive is EA-9013 sold by Borden Chemical Company, a Division of the Borden Company, New York, New York.

Reactive adhesive prepolymers, the other major category of suitable adhesives, are applied as a liquid at room temperature or moderately elevated temperatures and are then polymerized in situ to a relatively high molecular weight solid. The polymerization is by a variety of means including heat, radiation or the addition of a curing agent. Presently preferred adhesives are those containing acrylic monomers alone or in combination with acrylic oligomers. Suitable acrylic monomers or oligomers are butyl acrylate, 2-ethylhexyl acrylate, acrylic acid and a vinyl acetate. Suitable cross linking agents which may be applied in this adhesive system are multifunctional acrylates including pentaerythritol triacrylate, trimethylolpropane triacrylate. In addition, compounds such as benzoin ether or the like may be added to the liquid reactive mix and cross linking can then be accomplished by ultra-violet light. When the compound is to be cross linked by ultraviolet radiation the receptor is generally activated by a radiation source having a wave length range of 200–450 nanometers. A complete description of pressure sensitive adhesive products particularly directed to radiation curing and to suitable precursors can be found in "Radiation Curing of Pressure-Sensitive-Adhesive Products" by Andor Schwarcz presented at the 1976 SME conference on radiation curing. A discussion of ultraviolet sensitizers and cross linking agents is found in "The Design of UV-Curable Pressure-Sensitive Adhesives" by Carl Brock presented at the 1976 SME conference on radiation curing. The disclosures of both of these papers are hereby incorporated by reference, and are available through the Celanese Chemical Company, 1211 Avenue of the Americas, New York, New York 10036.

The choice of the particular oxidation resistant adhesive system is based upon the particular type of baffle employed. For example, if the water based, e.g. water emulsion adhesives are utilized, then the baffle must provide some mechanism for removing the water to allow for the adhesive to cure. This can be done by providing some measure of absorption in the baffle or some level of porosity which provides for evaporation. A baffle which has a garment facing layer of a foamed material such as polyurethane or foamed polyester is suitable for use with this adhesive system. The embodiment shown in FIG. 1 has such a configuration. According to FIG. 1, an absorbent layer 10 is rounded on the top and sides by wrap 11 and a bottom foam member 13 is employed. The foams offer some small absorptive capacity and by placing the liquid water emulsion adhesive 12 in selected foam cells the water component is evaporated or absorbed due to the porosity of the foam cell walls and the adhesive is partially shielded from air exposure due to its location. When the napkin is used, the foam is compressed and the adhesive exposed to the undergarment. It may be necessary in this case to have a two component baffle if the desired foam is not a complete moisture barrier at its top surface. A thin polyethylene or polypropylene sheet 15 is placed between the foam and the absorbent matrix to provide the necessary fluid impermeability.

Foams to be suitable adhesive carriers for purposes of this invention must be open celled and compressible with controlled hysteresis. Compressive strength is a function of void volume and density as well as compression and is measured by a Compression-Load-Deflection test. This test is a quantification of the load force necessary to produce 25% compression over the entire top area of the foam sample. For purposes of this invention, a range of 3 to 140 kPa is suitable with the lower ranges preferred. A value of 7 kPa is currently believed to be optimum.

Controlled resiliency is also desired for purposes of this invention. If there is complete "bounce back" the napkin having the foam will become disengaged. If the foam is compressed 50% then rebound of 10–50% is preferred. In other words, if the foam uncompressed has a value of 100%, compression of 50% with a 50% rebound produces a value of 75%.

The embodiment depicted at FIG. 2 is identical to that shown in FIG. 1 except that an undergarment facing surface or layer of the baffle be made of a relatively densely packed mat of fibers 14. If the fibers are water absorbent or have sufficient space between them for water evaporation the mat would be suitable for use with a water based adhesive according to that particular embodiment. A fibrous mat of, e.g. polyester, polypropylene, polyethylene, etc. could be used in this manner. Densities are not as critical when the mat is utilized as opposed to the foam because densities are not an accurate indication of the available area for moisture removal if the mat is utilized with a water soluble adhesive.

In the event that a reactive adhesive prepolymer system is chosen, the choice of materials for the garment facing side of the baffle substantially increases. Both the fibrous mat and the foam options are available for utilization with the reactive adhesive prepolymers but, in addition, a standard conventional baffle material such as polypropylene or polyethylene cast in a somewhat thicker film 16 is made with dimpled indentations in selected areas and the adhesive applied in these indentations. Another alternative is to selectively layer suitable adhesive on the garment facing side of the baffle and overlay with a foraminous layer.

As can be seen from the above embodiments, a variety of different combinations can be employed utilizing the idea of a geometrically sheltered adhesive having enhanced antioxident properties to provide a sanitary napkin in which a release liner is not needed.

What is claimed is:

1. A sanitary napkin including an absorbent matrix and a fluid impervious baffle having an irregularly contoured undergarment facing surface including recessed areas, said recessed areas containing pressure sensitive adhesive with an outward surface having substantial resistance to aging, and said adhesive surface exposed only when the napkin is flexed, said napkin manufactured without a separate disposable component for shielding said adhesive.

2. The napkin according to claim 1 wherein the undergarment facing surface permits moisture removal from the adhesive-containing areas and the adhesive is water containing.

3. The napkin according to claim 2 in which the adhesive is a water emulsion type.

4. The napkin according to claims 2 or 3 wherein the adhesive is an acrylic water-based dispersion.

5. The napkin according to claims 2 or 3 wherein the adhesive is a copolymer of vinyl acetate and 2-ethylhexyl acrylate in aqueous dispersion.

6. The napkin according to claim 1 wherein the undergarment facing surface is essentially nonabsorbent and nonmoisture conducting and the polymer is of the reactive adhesive polymer.

7. The napkin according to claim 6 in which the adhesive comprises acrylic monomers and the acrylic oligomers.

8. The napkin according to claim 6 wherein the adhesive is cured by ultraviolet radiation and contains an ultraviolet sensitive compound.

9. The napkin according to claim 8 wherein the ultraviolet sensitive compound is a benzoin ether.

10. The napkin according to claim 6 wherein the adhesive contains at least one cross linking agent.

11. The napkin according to claims 6, 7 or 10 in which the adhesive contains a multifunctional acrylate.

12. The napkin according to claims 1, 2, 3 or 6 wherein the baffle has a foam as the irregularly contoured adhesive surface.

13. The napkin according to claims 1, 2, 3 or 6 wherein the napkin has a densely packed mat of fiber as the irregularly contoured adhesive surface.

* * * * *